US010058309B2

(12) United States Patent
Hatta et al.

(10) Patent No.: US 10,058,309 B2

(45) Date of Patent: Aug. 28, 2018

(54) MEDICAL INSTRUMENT AND MEDICAL SYSTEM

(71) Applicant: TERUMO KABUSHIKI KAISHA, Tokyo (JP)

(72) Inventors: Tomonori Hatta, Kanagawa (JP); Wataru Karino, Kanagawa (JP); Taiga Nakano, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 152 days.

(21) Appl. No.: 14/432,002

(22) PCT Filed: Sep. 27, 2012

(86) PCT No.: PCT/JP2012/074920

§ 371 (c)(1),
(2) Date: Mar. 27, 2015

(87) PCT Pub. No.: WO2014/049783

PCT Pub. Date: Apr. 3, 2014

(65) Prior Publication Data

US 2015/0289857 A1 Oct. 15, 2015

(51) Int. Cl.

*A61B 10/00* (2006.01)
*A61B 10/02* (2006.01)

(Continued)

(52) U.S. Cl.

CPC ...... *A61B 10/0283* (2013.01); *A61B 10/0051* (2013.01); *A61B 10/0233* (2013.01);

(Continued)

(58) Field of Classification Search

CPC .. A61M 5/3202; A61M 5/158; A61M 5/3298; A61M 5/46; A61M 2005/1585;

(Continued)

(56) References Cited

U.S. PATENT DOCUMENTS 4,022,191 A * 5/1977 Jamshidi ............ A61B 10/0283 600/566
5,127,916 A * 7/1992 Spencer ................. A61B 90/39 606/185

(Continued)

*Primary Examiner* — Rene Towa
*Assistant Examiner* — May Abouelela

(57) ABSTRACT

Disclosed herein is a medical instrument used for harvesting biological tissues of a predetermined biological organ and a medical system. The medical instrument includes: a main body portion that has an elongated shape and has a distal part having a helical groove formed in an outer surface, a fluid lumen through which fluid is allowed to flow and pass, and a through-hole communicating with the fluid lumen and the outer surface of the distal part, at least part of the distal part being stuck into the biological organ; and a tubular member that has an insertion lumen into which the main body portion is inserted movably in axial direction and forms a gap through which fluid is allowed to flow and pass between the main body portion and the tubular member in a state in which the main body portion is inserted in the insertion lumen. The medical system includes: the medical instrument; a fluid supply unit that supplies a fluid into the fluid lumen of the main body portion; and a fluid drawing unit that draws the fluid existing in the gap.

7 Claims, 8 Drawing Sheets

21 22 20 35 25 31 30 C

(51) Int. Cl.
*A61B 17/00* (2006.01)
*A61B 17/3207* (2006.01)

(52) U.S. Cl.
CPC .................. *A61B 17/00234* (2013.01); *A61B 17/320758* (2013.01); *A61B 10/0275* (2013.01); *A61B 2010/0208* (2013.01); *A61B 2017/00309* (2013.01); *A61B 2017/00809* (2013.01); *A61B 2217/005* (2013.01); *A61B 2217/007* (2013.01)

(58) Field of Classification Search
CPC ............ A61B 17/3468; A61B 17/0469; A61B 10/0266; A61B 10/0275; A61B 17/00234; A61B 17/0218; A61B 2017/06076; A61B 5/150732
USPC .................................................. 600/562–567
See application file for complete search history.

(56) References Cited

U.S. PATENT DOCUMENTS 5,234,426 A * 8/1993 Rank .................. A61B 17/3403 604/164.06
5,490,521 A * 2/1996 Davis ................... A61B 8/0833 600/458
5,522,398 A * 6/1996 Goldenberg ......... A61B 10/025 600/562
6,015,391 A * 1/2000 Rishton .............. A61B 10/0266 600/562
6,019,776 A * 2/2000 Preissman .......... A61B 17/3472 600/567
7,722,549 B2 * 5/2010 Nakao ................ A61B 10/0266 600/564
7,828,746 B2 * 11/2010 Teague ............... A61B 10/0266 600/562
7,938,842 B1 * 5/2011 Chin ................ A61B 17/00008 604/104
7,988,643 B2 * 8/2011 Hoffmann ............ A61B 10/025 600/562
8,002,733 B2 * 8/2011 Kraft .................... A61B 10/025 600/565
8,162,851 B2 * 4/2012 Heske ................ A61B 10/0283 600/562
9,295,487 B2 * 3/2016 Miller .............. A61B 17/32002
9,326,784 B2 * 5/2016 Ravikumar
2004/0054377 A1 * 3/2004 Foster .................... A61B 10/04 606/167
2004/0267154 A1 * 12/2004 Sutton .................. A61B 10/025 600/562
2007/0219460 A1 * 9/2007 Goldenberg ....... A61B 10/0283 600/566
2008/0071193 A1 * 3/2008 Reuber .............. A61B 10/0275 600/567
2008/0177200 A1 * 7/2008 Ikehara ................ A61B 10/025 600/567
2008/0281223 A1 * 11/2008 Goldenberg ....... A61B 10/0266 600/567
2009/0204020 A1 * 8/2009 Miller ................ A61B 10/0041 600/563
2010/0228147 A1 * 9/2010 Suda ...................... A61B 10/04 600/567
2010/0280407 A1 * 11/2010 Polster ............... A61B 10/0266 600/566
2011/0224575 A1 * 9/2011 Carrillo, Jr. ........ A61B 10/0233 600/566

* cited by examiner 43
63
26
27
36
37
84
83
80
82
81
23
20
30
31
6A
70

MEDICAL INSTRUMENT AND MEDICAL SYSTEM

CROSS-REFERENCE TO RELATED APPLICATIONS

This application is based on International Application No. PCT/JP2012/074920 filed on Sep. 27, 2012. The entire contents of each and every foregoing application are incorporated herein by reference.

BACKGROUND

The present invention relates to a medical instrument used for harvesting biological tissues and a medical system including the medical instrument.

Biopsy techniques, in which biological tissues are harvested from a lesion site of a patient and tested in order to make a diagnosis of the disease condition of the patient, are widely known. The harvesting of biological tissues is carried out by introducing a biopsy instrument having a diameter set small, such as biopsy forceps or a biopsy needle, into a living body under an image captured by an imaging device such as an endoscope and subsequently performing puncture with the biopsy instrument to a target site to harvest biological tissues. Therefore, it is preferable for the biopsy instrument to have a structure with enhanced puncture performance so that puncture can be easily performed into biological tissues, and a biopsy needle or the like in which a helical groove is formed at the distal end has been developed for example (such as described, for example, in Japanese Patent Laid-Open No. 2007-275175).

On the other hand, in some cases, it is preferable to make a diagnosis based on as many biological tissues as possible to obtain an accurate diagnosis result in the case of making a definitive diagnosis of a disease by a biopsy technique. Therefore, plural times of puncture to a target site are often carried out in order to ensure more biological tissues. However, it is not preferable to unnecessarily increase the number of times of puncture in terms of the invasiveness and the working efficiency.

SUMMARY

According to the biopsy needle described in the above-described Japanese Patent Laid-Open No. 2007-275175, puncture work itself can be smoothly performed because the puncture performance is improved. However, when biological tissues are collected after the puncture, the biopsy needle needs to be temporarily brought out to the external of the living body. Therefore, work of introducing the biopsy needle into the living body and work of performing puncture to the target site need to be performed plural times if it is impossible to ensure the necessary amount of biological tissues by one time of puncture. Thus, there is a problem that it is impossible to harvest biological tissues with low invasiveness and high efficiency.

Therefore, the present disclosure is provided in order to solve the above-described problem and an intent thereof is to provide a medical instrument that can harvest a desired amount of biological tissues with low invasiveness and high efficiency.

According to modes of the present disclosure, the following configurations are provided.

(1) There is provided a medical instrument used for harvesting biological tissues of a predetermined biological organ. The medical instrument includes a main body portion that has an elongated shape and has a distal part having a helical groove formed in an outer surface, a fluid lumen through which fluid is allowed to flow and pass, and a through-hole communicating with the fluid lumen and the outer surface of the distal part. At least part of the distal part is stuck into the biological organ. The medical instrument further includes a tubular member that has an insertion lumen into which the main body portion is inserted movably in an axial direction and forms a gap through which fluid is allowed to flow and pass between the main body portion and the tubular member in a state in which the main body portion is inserted in the insertion lumen.

(2) The medical instrument according to the above (1), wherein the biological tissues adhering to the helical groove are allowed to be collected by drawing a fluid flowing in the gap while supplying the fluid into the fluid lumen to make the fluid flow into the gap via the through-hole.

(3) The medical instrument according to the above (1), further having a positioning portion that is disposed between an outer surface of the main body portion and the tubular member and defines relative positions of the main body portion and the tubular member in a radial direction.

(4) The medical instrument according to the above (1), further having a holding portion that holds the main body portion movably relative to the tubular member.

(5) The medical instrument according to the above (4), wherein the holding portion has a first screw part provided on the main body portion and a second screw part that is provided on the tubular member and is meshed with the first screw part, and rotating the main body portion or the tubular member allows the main body portion to be moved in the axial direction with an amount of movement according to an amount of rotation.

(6) The medical instrument according to the above (1), wherein the medical instrument is a medical instrument used for harvesting biological tissues in a respiratory region.

(7) A medical system has the medical instrument according to the above (1), a fluid supply unit that supplies a fluid into the fluid lumen of the main body portion, and a fluid drawing unit that draws the fluid existing in the gap.

According to the mode described in the above (1), in collection of the biological tissues adhering to the helical groove formed in the main body portion stuck into the biological organ, the biological tissues can be floated up from the main body portion by the fluid supplied into the fluid lumen of the main body portion and these biological tissues can be collected on the proximal side of the medical instrument via the gap formed between the main body portion and the tubular member. Because work of bringing out the main body portion to the external of the living body does not need to be performed in the collection of the biological tissues, a desired amount of biological tissues can be harvested without repeating work of guiding the medical instrument to the biological organ and work of puncture with the main body portion into the biological organ plural times. Therefore, the biological tissues can be harvested with low invasiveness and high efficiency compared with the case of using related-art medical instruments for a biopsy.

Furthermore, according to the mode described in the above (2), the medical instrument is so configured as to collect the biological tissues by drawing the fluid flowing in the gap while supplying the fluid into the fluid lumen to make the fluid flow into the gap via the through-hole. Therefore, it is possible to surely collect the biological tissues adhering to the helical groove formed at the distal part of the main body portion.

In addition, according to the mode described in the above (3), the medical instrument is so configured as to have the positioning portion that defines the relative positions of the main body portion and the tubular member in the radial direction. Therefore, the size of the gap formed between the main body portion and the tubular member can be properly ensured and the fluid and the biological tissues can be smoothly moved in the gap.

Moreover, according to the mode described in the above (4), the medical instrument is so configured as to have the holding portion that holds the main body portion movably relative to the tubular member. Therefore, introduction into a living body can be performed in the state in which the main body portion is integrally assembled with the tubular member. Furthermore, only the main body portion can be independently moved in puncture into the biological organ with the main body portion. Thus, the medical instrument with high usability can be provided.

Furthermore, according to the mode described in the above (5), the holding portion is formed of the first screw part provided on the main body portion and the second screw part provided on the tubular member. Therefore, rotating the main body portion or the tubular member allows the main body portion to be moved in the axial direction with the amount of movement according to the amount of rotation. Because it is possible to easily adjust the amount of movement through operation at hand, the medical instrument with higher usability can be provided.

In addition, according to the mode described in the above (6), also in the case in which the medical instrument is used to harvest biological tissues in the respiratory region, the main body portion can be favorably stuck into an organ in the respiratory region formed of comparatively-soft biological tissues. Furthermore, because the number of times of bringing out the main body portion to the external of the living body can be suppressed to a small number, e.g. in the case of harvesting biological tissues at a peripheral part of a lung, the work time can be shortened at a higher degree compared with the case of using related-art medical instruments for a biopsy.

Moreover, according to the mode described in the above (7), the medical system including the medical instrument, the fluid supply unit that supplies a fluid into the fluid lumen of the main body portion, and the fluid drawing unit that draws the fluid existing in the gap formed between the main body portion and the tubular member is constructed. Therefore, a medical system to efficiently harvest the biological tissues by using the medical instrument can be provided.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

DETAILED DESCRIPTION OF THE PREFERRED EMBODIMENT

The present invention will be described below through an embodiment with reference to the respective drawings. Note that the dimensional ratio of the drawings is exaggerated for convenience of explanation and is different from the actual ratio in some cases.

FIGS. 1 to 6 are diagrams for explaining the configurations of a medical instrument and a medical system according to the present embodiment. In FIGS. 2 to 5, sections in the axial direction of the medical instrument are shown in an enlarged manner. FIGS. 7 to 10 are diagrams for explaining a usage example of the medical instrument and the medical system according to the present embodiment.

Figure 1:
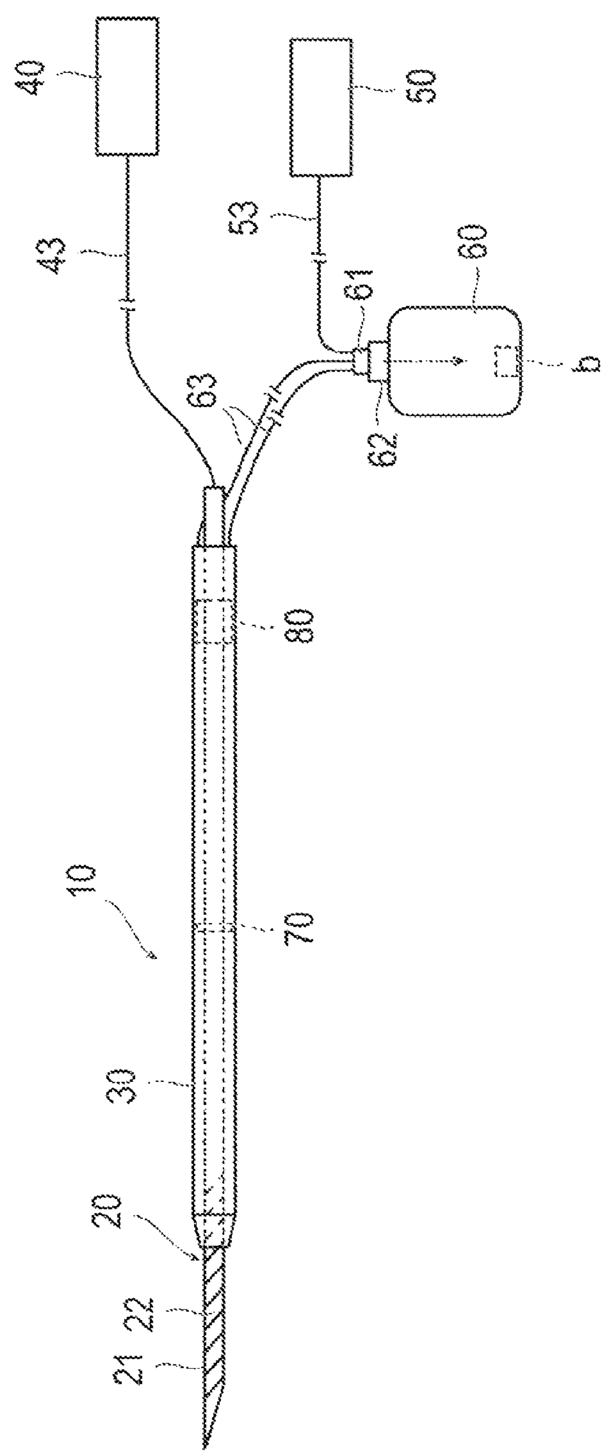
FIG. 1 is a diagram showing, in a simplified manner, the overall configuration of a medical instrument and a medical system according to an embodiment of the present invention.
Figure 2:
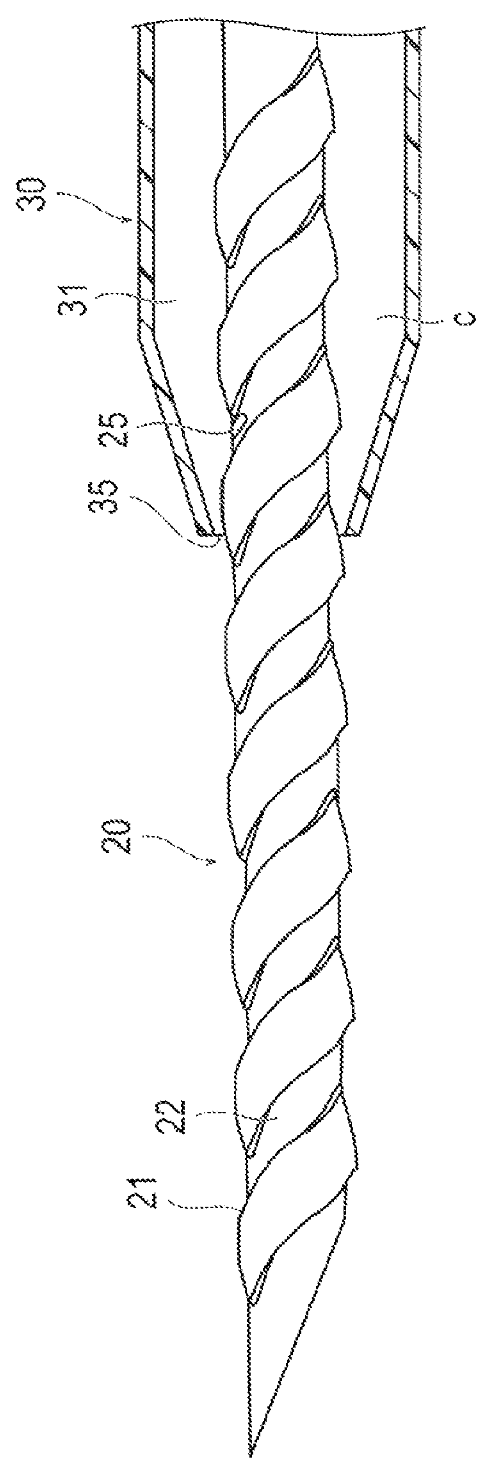
FIG. 2 is a sectional view for explaining the configurations of a main body portion and a tubular member included in the medical instrument according to the embodiment and is an enlarged view of a section of the distal side of the tubular member.
Figure 3:
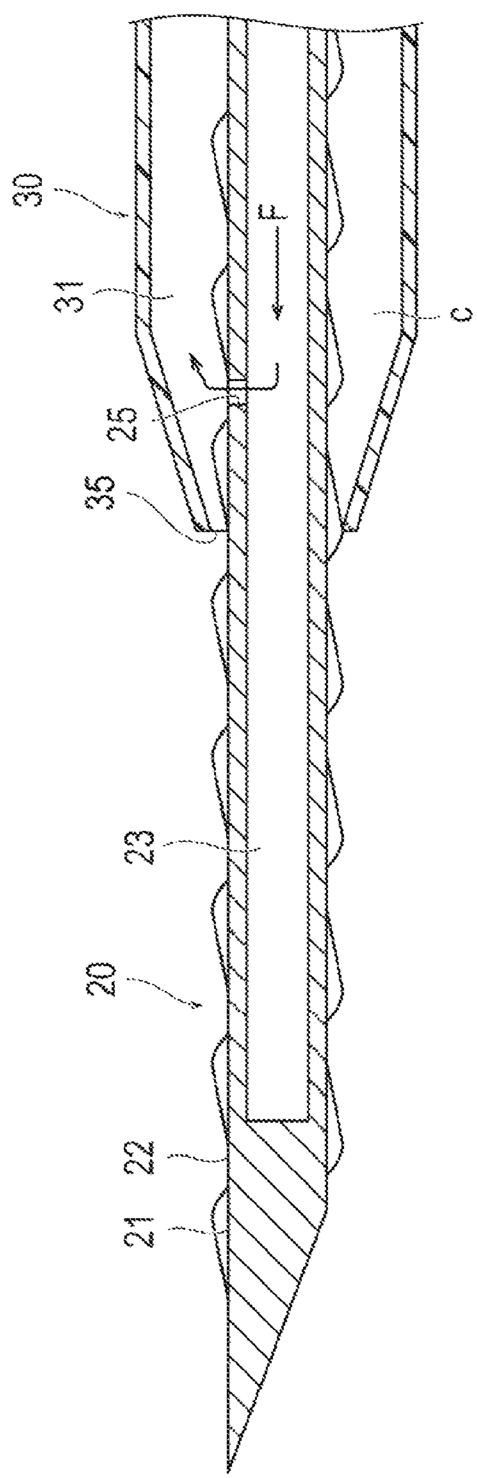
FIG. 3 is a sectional view for explaining the configurations of the main body portion and the tubular member included in the medical instrument according to the embodiment and is an enlarged view of a section of the distal side of the main body portion and the tubular member.

Referring to FIGS. 1 to 3, in an outline, a medical instrument 10 according to the present embodiment is the medical instrument 10 used for harvesting biological tissues of a predetermined biological organ and has a main body portion 20 having an elongated shape and a tubular member 30 into which this main body portion 20 with an elongated shape can be inserted. Furthermore, the medical instrument 10 can be used together with a fluid supply unit 40 that supplies a fluid to the medical instrument 10 and a fluid drawing unit 50 that draws the fluid flowing at a predetermined site of the medical instrument 10, and a medical system 100 for harvesting biological tissues can be configured by the medical instrument 10, the fluid supply unit 40, and the fluid drawing unit 50.

The respective configurations of the medical instrument 10 and the medical system 100 will be described in detail below. In the description of the specification, the tip side toward which the main body portion 20 and the tubular member 30 are extended (left side in FIG. 1) will be referred to as the distal side of the medical instrument 10 and the opposite side thereto will be referred to as the proximal side of the medical instrument 10 (right side in FIG. 1). Furthermore, the axial direction refers to the direction along which the main body portion 20 and the tubular member 30 are extended, i.e. the left-right direction in FIG. 1.

As shown in FIGS. 2 and 3, the main body portion 20 of the medical instrument 10 has a distal part 21 having a helical groove 22 formed in the outer surface of the main body portion 20, a fluid lumen 23 through which fluid can flow and pass, and a through-hole 25 communicating with the fluid lumen 23 and the outer surface of the distal part 21, and is so configured that at least part of the distal part 21 is stuck into a biological organ B (see FIGS. 7 to 10).

The helical groove 22 can be formed across a predetermined range on the distal part 21 of the main body portion 20. Although the helical groove 22 is formed to make a right-hand turn around the axis of the main body portion 20, it is also possible to form it to make a left-hand turn. The range of formation of the helical groove 22 is not particularly limited and can be designed in consideration of the puncture depth of puncture into the biological organ B with the distal part 21. Similarly, the pitch of the groove can also be changed as appropriate in consideration of the performance of puncture into the biological organ. For example, the pitch of the groove can be set small in order to allow puncture with the main body portion 20 into a comparatively-hard biological organ. Furthermore, a bevel for cutting off biological tissues is made at the distalmost end of the groove 22 although diagrammatic representation thereof is omitted.

The distal end part of the main body portion 20 can be formed into a sharp needle shape as shown in the diagram in order to further improve the performance of puncture into the biological organ B. It is also possible for the distal end part to be formed into a shape such as a rectangular shape, a shape protruding in a curving manner, or a taper shape instead of being formed into such a needle shape.

The fluid lumen 23 of the main body portion 20 is so made as to enable a fluid supplied from the fluid supply unit 40 to flow and pass through it. The fluid lumen 23 is extended along the axial direction of the main body portion 20 and communicates with a proximal opening 26 made at the proximal end of the main body portion 20 (see FIG. 5). A fluid tube 43 joined to the fluid supply unit 40 can be joined to the proximal end of the fluid lumen 23 of the main body portion 20.

At the position at which the fluid tube 43 is joined in the fluid lumen 23, a port 27 that prevents the leakage of fluid from the proximal opening 26 and allows the fluid tube 43 to be joined to the main body portion 20 can be provided. As this port 27, e.g. a seal member formed of an elastic member or the like can be used. Furthermore, in this seal member, e.g. a connection hole (not shown) for connecting the fluid tube 43 by fitting or the like can be made.

The through-hole 25 made in the main body portion 20 can be formed into a circular shape for example. However, the shape thereof is not particularly limited and it is also possible to form it into a rectangular shape, a triangular shape, or another polygonal shape. Furthermore, the number of through-holes 25 is not limited to one and may be two or more, and the position at which it is made is also not particularly limited. Making this through-hole 25 allows a fluid supplied into the fluid lumen 23 of the main body portion 20 to flow out to the external of the fluid lumen 23, i.e. to the outer surface of the main body portion 20.

It is preferable that a material having predetermined rigidity is used as the material to form the main body portion 20 so that the distal part 21 of the main body portion 20 can be stuck and penetrate into a biological organ. As such a material, e.g. a metal, hard resin, ceramic, or the like can be used.

The tubular member 30 has an insertion lumen 31 into which the main body portion 20 is inserted movably in the axial direction. Furthermore, in a state in which the main body portion 20 is inserted in the insertion lumen 31 of the tubular member 30, a gap c through which fluid can flow and pass is formed between the tubular member 30 and the main body portion 20. This gap c is formed based on the dimensional difference between the outer diameter of the main body portion 20 and the inner diameter of the tubular member 30.

A material having flexibility suffices as the material to form the tubular member 30. For example, a material similar to the materials of guide sheaths and catheter tubes that are publicly known in the medical field can be used. As one example, polyolefin such as polyethylene, polypropylene, ethylene-propylene copolymer, or ethylene-vinyl acetate copolymer or a thermoplastic resin such as soft polyvinyl chloride can be used.

Figure 5:
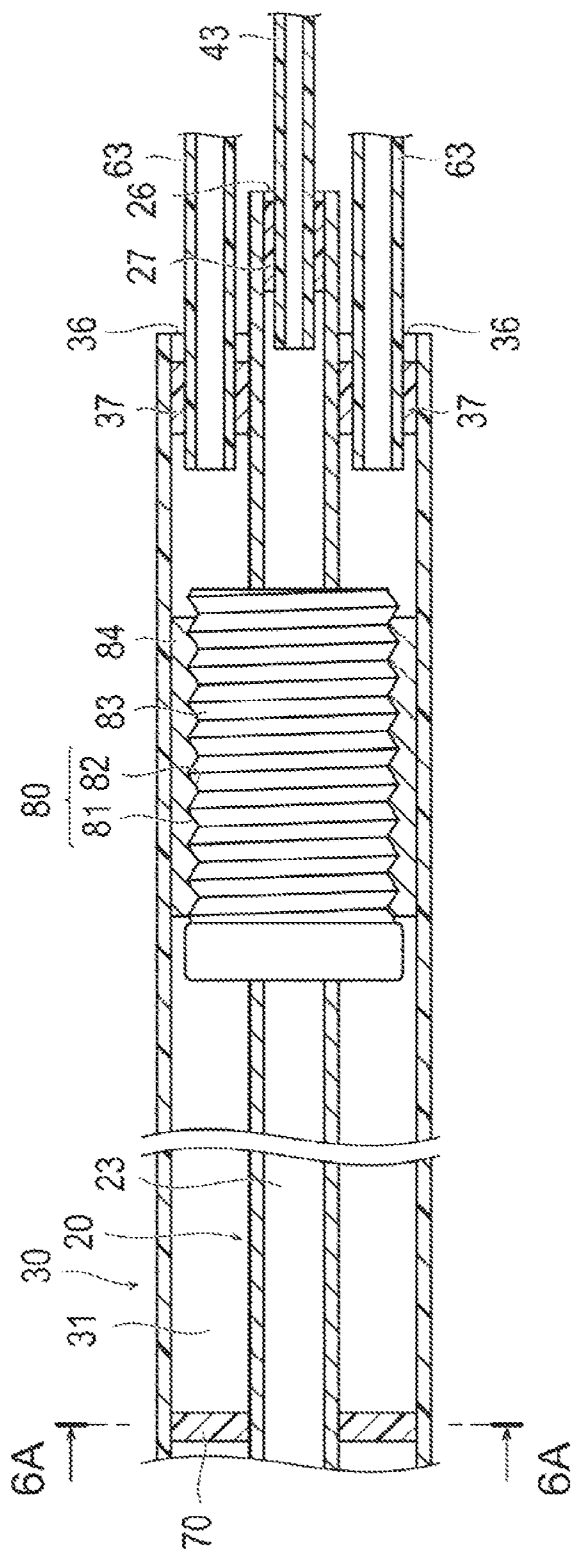
FIG. 5 is a sectional view for explaining the configurations of a positioning portion and a holding portion included in the medical instrument according to the embodiment and is an enlarged view of a section of the proximal side of the main body portion and the tubular member.

The insertion lumen 31 of the tubular member 30 is extended along the axial direction as with the fluid lumen 23 of the main body portion 20 and communicates with a distal opening 35 made at the distal end of the insertion lumen 31 and a proximal opening 36 made at the proximal end of the insertion lumen 31 (see FIG. 5). Furthermore, fluid tubes 63 led out from a housing container 60 to be described later can be joined to the proximal end of the insertion lumen 31.

At the position at which the fluid tubes 63 are joined in the insertion lumen 31, a port 37 to which the fluid tubes 63 can be joined can be provided. As this port 37, one having a configuration similar to that of the port 27, which joins the main body portion 20 and the fluid tube 43, can be used. The number of set fluid tubes 63 is not particularly limited. For example, two fluid tubes 63 can be connected at different positions in the circumferential direction as shown in the diagram.

Referring to FIGS. 2 and 3, the flow of a fluid flowing in the respective lumens 23 and 31 will be described. The fluid supplied from the fluid supply unit 40 is made to flow into the fluid lumen 23 of the main body portion 20 via the fluid tube 43 (the flow of the fluid is shown by an arrow F). Then, the fluid passes through the through-hole 25 formed in the main body portion 20 and flows to the external of the main body portion 20. At this time, if the main body portion 20 is in the state of being inserted in the insertion lumen 31 of the tubular member 30 and the through-hole 25 is located in the insertion lumen 31 of the tubular member 30, the fluid flows into the insertion lumen 31 of the tubular member 30, i.e. into the gap c between the main body portion 20 and the tubular member 30. As described later, by this flow of the fluid, biological tissues b adhering to the helical groove 22 of the main body portion 20 can be made to float up from the main body portion 20 (see FIG. 10).

Figure 4:
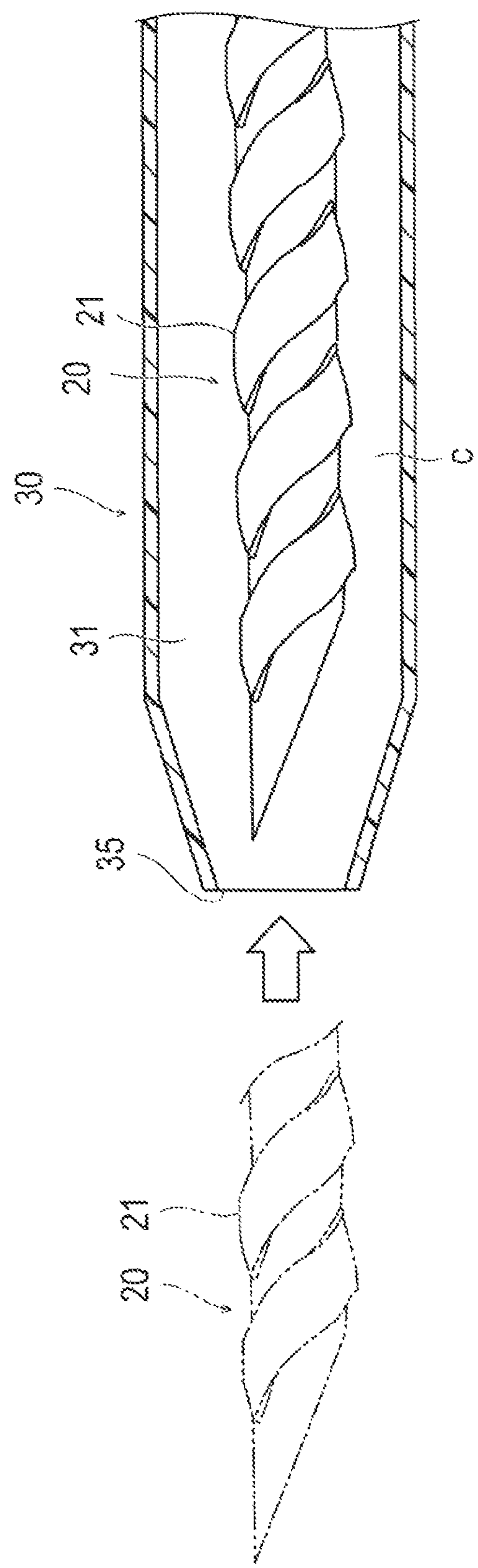
FIG. 4 is a sectional view showing how the main body portion included in the medical instrument according to the embodiment is inserted into an insertion lumen of the tubular member.

As shown in FIG. 4, the main body portion 20 can be inserted into the insertion lumen 31 of the tubular member 30 via the distal opening 35 made at the distal part of the tubular member 30. Furthermore, by moving the main body portion 20 along the axial direction of the tubular member 30 in the inserted state, the distal part 21 of the main body portion 20 can be protruded from the distal opening 35 of the tubular member 30. The movement of the main body portion 20 along the axial direction can be carried out by pushing and pulling of the proximal end of the main body portion 20 through operation at hand by the user who uses the medical instrument 10 for example. Furthermore, to enable the pushing and pulling of the main body portion 20 by operation at hand, for example the length of the main body portion 20 in the axial direction can be set to such a length that the proximal end of the main body portion 20 is led out from the proximal opening 36 of the tubular member 30 in the state in which the distal part 21 of the main body portion 20 is inserted in the insertion lumen 31 of the tubular member 30. When the distal part 21 of the main body portion 20 is stuck into the biological organ B, operation of making the whole of the main body portion 20 advance while rotating it is carried out so that the distal part 21 may be screwed to a target site of the biological organ B for example.

The distal part of the tubular member 30 can be formed into e.g. a taper shape in which the diameter becomes smaller toward the distal side. Giving such a shape makes it possible to smoothly perform introduction into a living body and movement in the living body.

The diameter of the distal opening 35 of the tubular member 30 can be set slightly larger or equivalent to the outer diameter of the distal part 21 of the main body portion 20. Employing such a configuration can prevent a situation in which the diameter of the distal opening 35 of the tubular member 30 becomes too large relative to the outer diameter of the distal part 21 of the main body portion 20 and the fluid flowing into the gap c leaks out from the distal opening 35. Furthermore, it is possible to prevent a situation in which the diameter of the tubular member 30 becomes too small with respect to the outer diameter of the distal part 21 of the main body portion 20 and, when being moved to advance or retreat, the main body portion 20 gets caught on the tubular member 30 to become incapable of being smoothly moved.

As the fluid supply unit 40, a component that can pump various kinds of fluids into the fluid lumen 23 of the main body portion 20 can be used and e.g. a publicly-known fluid pump can be used. As the fluid supplied from the fluid supply unit 40, a gas or a liquid can be used and e.g. air or a physiological saline can be used. As the fluid tube 43, a component that allows fluid to flow and pass through it and can connect the fluid supply unit 40 to the main body portion 20 liquid-tightly and gas-tightly can be used. For example, a publicly-known resin tube having flexibility can be used.

The fluid drawing unit 50 is so configured as to be capable of drawing various kinds of fluids supplied from the fluid supply unit 40. As the fluid drawing unit 50, e.g. a publicly-known fluid pump can be used as with the fluid supply unit 40. As shown in FIG. 1, the fluid drawing unit 50 is connected to the housing container 60 for housing the biological tissues b via a predetermined fluid tube 53.

As the housing container 60, e.g. a component formed of a hard resin, glass, metal, or the like can be used. The housing container 60 can be so configured as to have a connecting part 61 that can connect the fluid tubes 53 and 63 liquid-tightly and gas-tightly. This connecting part 61 can be provided on a lid 62 that is so configured as to be capable of hermetically sealing the inside of the housing container 60 for example. Furthermore, the connecting part 61 can be formed by e.g. a mechanical connecting port that can connect the respective fluid tubes 53 and 63 by screwing or insertion.

The fluid tubes 63 are so connected as to make the insertion lumen 31 of the tubular member 30 communicate with the inside of the housing container 60. Furthermore, the fluid tube 53 is so connected as to make the inside of the housing container 60 communicate with the fluid drawing unit 50. When drawing operation by the fluid drawing unit 50 is carried out, the fluid existing in the insertion lumen 31 of the tubular member 30 flows into the housing container 60. Furthermore, together with this fluid flowing into the housing container 60, the biological tissues b adhering to the helical groove 22 of the main body portion 20 can be made to move in the gap c between the main body portion 20 and the tubular member 30 and flow into the housing container 60 (see FIG. 10).

As the respective fluid tubes 53 and 63, components having a configuration similar to that of the fluid tube 43, which connects the fluid lumen 23 of the main body portion 20 to the fluid supply unit 40, can be used. However, as the fluid tubes 63, which connect the tubular member 30 to the housing container 60, components having a diameter set to such magnitude as to allow the biological tissues b to flow and pass therethrough are used.

Figure 6:
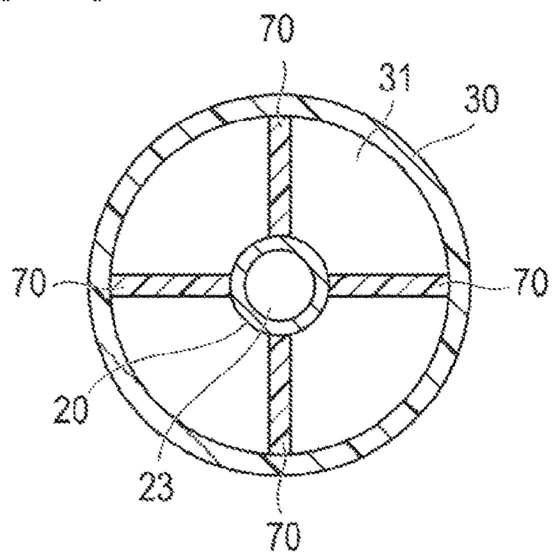
FIG. 6 is a sectional view showing, in an enlarged manner, a section along line 6A-6A shown in FIG. 5.

As shown in FIGS. 5 and 6, the medical instrument 10 can be so configured as to have a positioning portion 70 that defines the relative positions of the main body portion 20 and the tubular member 30 in the radial direction. The positioning portion 70 is disposed between the main body portion 20 and the tubular member 30.

The positioning portion 70 can be formed by e.g. a component that positions and disposes the main body portion 20 and the tubular member 30 in such a manner that the axial core of the main body portion 20 corresponds with the axial core of the tubular member 30. This positioning portion 70 can be so disposed as to be fixed to one of the main body portion 20 and the tubular member 30 for example. The shape and material of the positioning portion 70 are so selected as to generate, between the main body portion 20 and the tubular member 30, such a friction force that the advancing and retreating movement of the main body portion 20 is not precluded due to the placement of the positioning portion 70. The shape is not particularly limited as long as it has such a shape as not to occlude the gap c formed between the main body portion 20 and the tubular member 30. For example, as shown in the diagram, the positioning portion 70 can be formed by a columnar member that supports the outer surface of the main body portion 20 and the inner surface of the tubular member 30. As the constituent material, e.g. a soft rubber material can be used.

In the medical instrument 10, four positioning portions 70 are disposed at different positions in the circumferential direction. By disposing plural positioning portions 70 at uniform intervals in the circumferential direction of the main body portion 20, the gap c having a uniform size can be formed between the main body portion 20 and the tubular member 30. However, the number of placed positioning portions 70 is not particularly limited and can be changed as appropriate.

The medical instrument 10 can be so configured as to have a holding portion 80 that holds the main body portion 20 movably relative to the tubular member 30. This holding portion 80 can be so configured as to have a first screw part 81 provided on the main body portion 20 and a second screw part 82 that is provided on the tubular member 30 and is meshed with the first screw part 81 for example. By providing the holding portion 80 with such a configuration, through rotating the main body portion 20 or the tubular member 30, the main body portion 20 can be moved in the axial direction with the amount of movement according to the amount of rotation.

In the medical instrument 10, the first screw part 81 included in the holding portion 80 is formed of a male screw made on the outer surface of a first member 83 attached to a predetermined site on the proximal side of the main body portion 20. This first member 83 can be so configured as to have a through-hole (not shown) penetrating in the axial direction so that blocking of the flow of the fluid in the insertion lumen 31 may be avoided. The second screw part 82 included in the holding portion 80 is formed of a female screw made on the outer surface of a second member 84 attached to a predetermined site on the proximal side of the tubular member 30. The pitch and axial length of each of the screw parts 81 and 82 can be changed as appropriate. Furthermore, it is also possible to provide the first screw part 81 on the side of the tubular member 30 and provide the second screw part 82 on the side of the main body portion 20. In operating the holding portion 80, it is also possible to move the tubular member 30 relative to the main body portion 20 by rotating the tubular member 30 without rotating the main body portion 20.

The medical system 100 can be so configured as to include a control measure including a central processing unit (CPU) in which a program to carry out operation control of the fluid supply unit 40 and the fluid drawing unit 50 is embedded in advance, and so forth. Such a control measure enables more precise control of various kinds of operation, such as start and end of operation of supplying and drawing a fluid and adjustment of the pressure.

Next, a method for harvesting the biological tissues b by using the medical instrument 10 and the medical system 100 will be described.

In the following description, a biological organ in the respiratory region (e.g. lung, bronchus, etc.) of a living body will be exemplified as the biological organ B as the target of harvesting of the biological tissues b. The biological tissues b as the harvesting target are e.g. biological tissues at a predetermined site of the biological organ B where a lesion such as a cancer seems to be caused. The harvested biological tissues b can be used for a biopsy technique for making a determination about the cancer.

Figure 7:
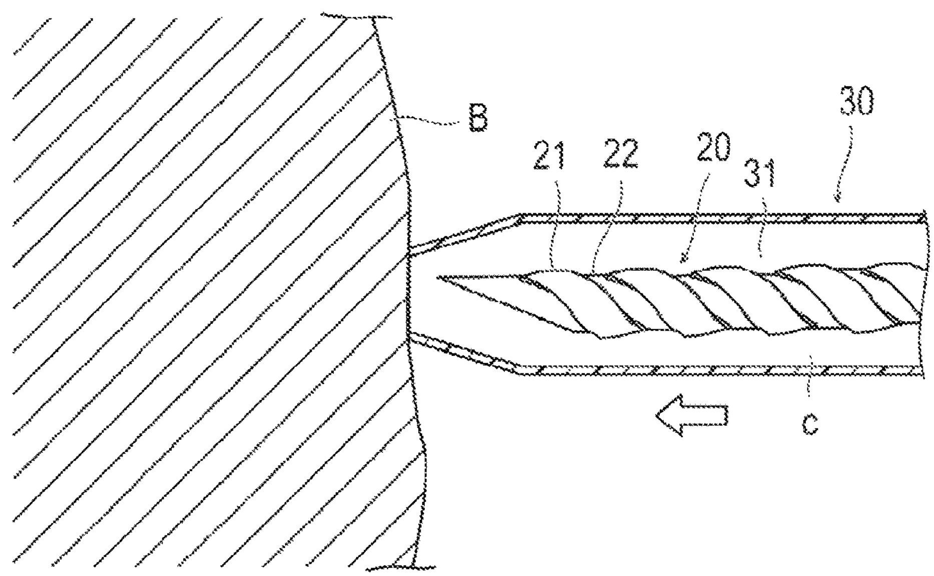
FIG. 7 is a diagram for explaining a usage example of the medical instrument according to the embodiment and is a diagram schematically showing a state in which the main body portion and the tubular member are brought close to the periphery of biological tissues as a harvesting target.

As shown in FIG. 7, the main body portion 20 is inserted into the insertion lumen 31 of the tubular member 30 to make a state in which the gap c is formed between the tubular member 30 and the main body portion 20. At this time, the distal part 21 of the main body portion 20 can be prevented from inadvertently getting contact with the respective parts of the living body by housing the distal part 21 of the main body portion 20 in the insertion lumen 31 of the tubular member 30.

Subsequently, the medical instrument 10 is introduced into the living body to be guided to the biological organ B. Prior to the introduction of the medical instrument 10, the route of the introduction of the medical instrument 10 can be checked in advance by using an imaging measure such as an endoscope, X-ray apparatus, or computerized tomography (CT) apparatus. Furthermore, it is also possible to introduce the medical instrument 10 while acquiring an image in the living body by the imaging measure. Moreover, it is also possible to introduce the medical instrument 10 in the living body through a channel provided in an endoscope or the like.

Figure 8:
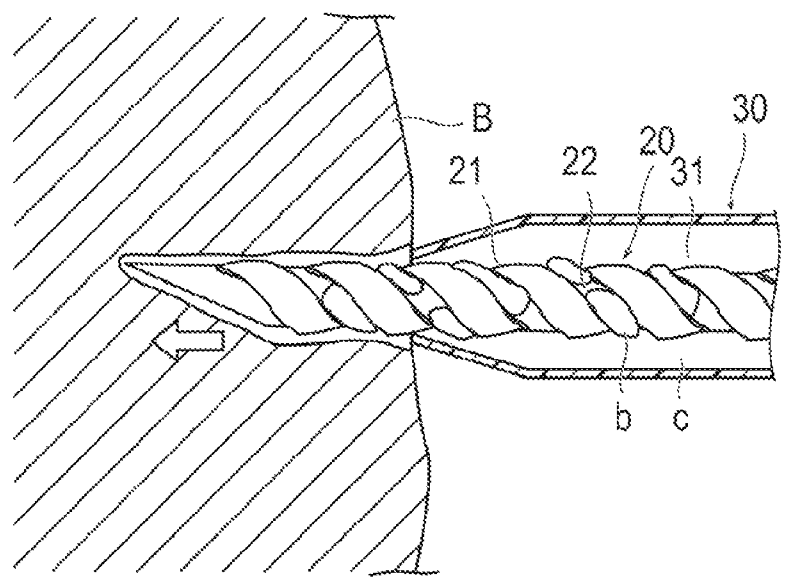
FIG. 8 is a diagram for explaining the usage example of the medical instrument according to the embodiment and is a diagram schematically showing a state in which a distal part of the main body portion is stuck into a biological organ in which the biological tissues as the harvesting target exist.

As shown in FIG. 8, the main body portion 20 is made to advance relative to the tubular member 30 and the distal part 21 of the main body portion 20 is protruded from the distal opening 35 of the tubular member 30. The action of making the main body portion 20 advance can be made by rotating the proximal end of the main body portion 20 through operation at hand. By making the main body portion 20 advance, the distal part 21 of the main body portion 20 is stuck to a target site of the biological organ B. Because the helical groove 22 is made at the distal part 21 of the main body portion 20, the main body portion 20 can be smoothly stuck into even an organ in the respiratory region formed of comparatively-soft biological tissues.

Figure 9:
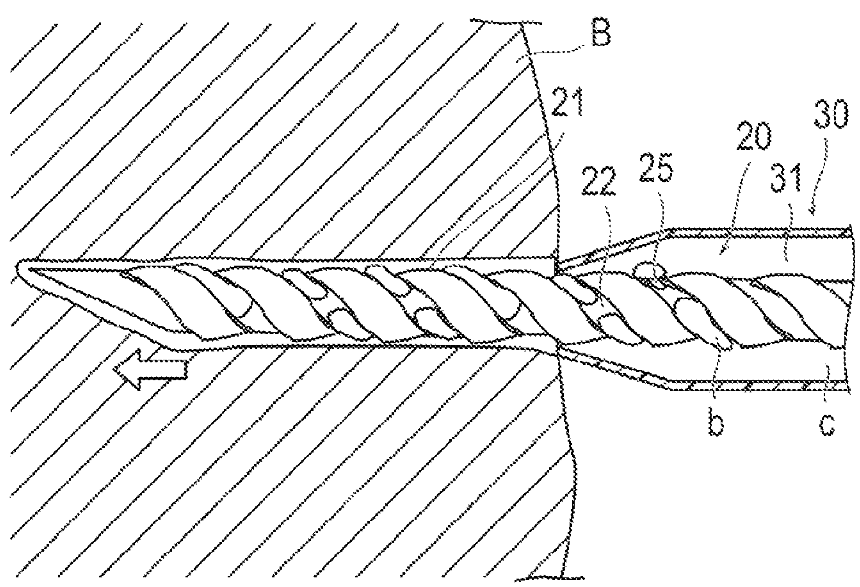
FIG. 9 is a diagram for explaining the usage example of the medical instrument according to the embodiment and is a diagram schematically showing a state in which the distal part of the main body portion is further stuck into the inside of the biological organ in which the biological tissues exist from the state shown in FIG. 8.

As shown in FIG. 9, the main body portion 20 is further moved to advance. The biological tissues b cut off by rotating the main body portion 20 adhere to the surface of the helical groove 22. These biological tissues b travel in the helical groove 22 to move toward the proximal side of the main body portion 20 in association with increase in the amount of puncture with the main body portion 20 into the biological organ B.

Figure 10:
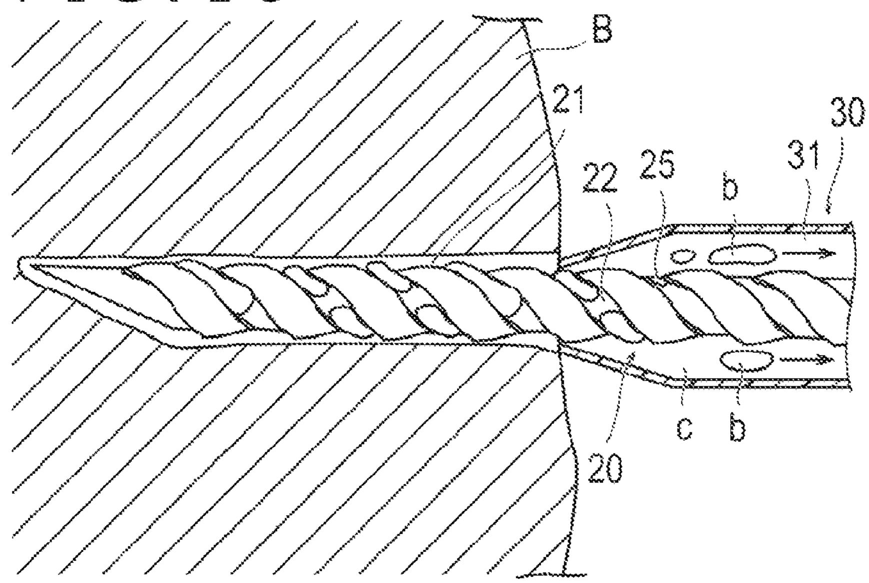
FIG. 10 is a diagram for explaining the usage example of the medical instrument according to the embodiment and is a diagram schematically showing how the biological tissues adhering to a helical groove of the main body portion are collected.

As shown in FIG. 10, when the biological tissues b adhering to the surface of the helical groove 22 have moved into the insertion lumen 31 of the tubular member 30, the fluid supply unit 40 is operated to supply a fluid into the fluid lumen 23 of the main body portion 20. The supplied fluid flows into the gap c between the main body portion 20 and the tubular member 30 via the through-hole 25 made in the main body portion 20. At this time, the biological tissues b adhering to the helical groove 22 of the main body portion 20 are floated up from the helical groove 22. Then, in the state in which the fluid is supplied into the fluid lumen 23 of the main body portion 20, the fluid drawing unit 50 is operated to draw the fluid and the biological tissues b flowing in the insertion lumen 31 of the tubular member 30. This operation can move the fluid and the biological tissues b to the proximal side of the insertion lumen 31. Then, the fluid and the biological tissues b that have moved to the proximal side of the insertion lumen 31 are made to flow into the housing container 60 via the fluid tubes 63 joined to the tubular member 30 (see FIG. 1).

In the case of harvesting the biological tissues b by using the medical system 100 at an atmospheric pressure, for example the fluid supply unit 40 and the fluid drawing unit 50 can be so operated as to set a positive pressure in the fluid lumen 23 of the main body portion 20 through supply of a fluid by the fluid supply unit 40 and set a negative pressure in the insertion lumen 31 of the tubular member 30. Setting the pressure in each of the lumens 23 and 31 in this manner makes it possible to surely float up the biological tissues b adhering to the helical groove 22 of the main body portion 20 from the main body portion 20 and harvest them. Thus, the harvesting can be carried out more efficiently.

In the case of continuously harvesting the biological tissues b, the main body portion 20 is further made to advance to the inside of the biological organ B. Then, after a desired amount of biological tissues b travel in the helical groove 22 to move into the insertion lumen 31 of the tubular member 30, the fluid supply unit 40 and the fluid drawing unit 50 are operated to collect the biological tissues b. In the case of using the medical instrument 10 in this manner, the work of collecting the biological tissues b can be continuously carried out without work of bringing out the main body portion 20 to the external of the living body.

As described above, the method for harvesting biological tissues by using the medical instrument has the following steps: a step (i) of inserting, into an insertion lumen of a tubular member, a main body portion that has an elongated shape and has a distal part having a helical groove formed in the outer surface, a fluid lumen through which fluid can flow and pass, and a through-hole communicating with the fluid lumen and the outer surface of the distal part to make a state in which a gap through which fluid can flow and pass is formed between the main body portion and the tubular member, and introducing the main body portion and the tubular member into a living body; a step (ii) of making the main body portion advance along the axial direction of the tubular member and performing puncture into a biological organ with the distal part of the main body portion; a step (iii) of supplying a fluid into the fluid lumen of the main body portion and making the fluid flow into the gap; and a step (iv) of drawing and collecting the fluid and biological tissues existing in the gap.

Furthermore, the method is characterized in that the above-described step (i) is carried out in a state in which the distal part of the main body portion is housed in the insertion lumen of the tubular member and the above-described step (iv) is carried out in a state in which the through-hole of the main body portion is located in the insertion lumen of the tubular member.

Moreover, the method is characterized by further having the following steps subsequent to the above-described step (iv): a step (v) of further making the main body portion advance into biological tissues; and a step (vi) of drawing and collecting the fluid and biological tissues existing in the gap while supplying the fluid into the fluid lumen.

As above, according to the medical instrument 10 in accordance with the present embodiment, in collection of the biological tissues b adhering to the helical groove 22 formed in the main body portion 20 stuck into the biological organ B, the biological tissues b can be floated up from the main body portion 20 by the fluid supplied into the fluid lumen 23 of the main body portion 20 and these biological tissues b can be collected on the proximal side of the medical instrument 10 via the gap c formed between the main body portion 20 and the tubular member 30. Because work of bringing out the main body portion 20 to the external of the living body does not need to be performed in the collection of the biological tissues b, a desired amount of biological tissues b can be harvested without repeating work of guiding the medical instrument 10 to the biological organ B and work of puncture with the main body portion 20 into the biological organ B plural times. Therefore, the biological tissues b can be harvested with low invasiveness and high efficiency compared with the case of using related-art medical instruments for a biopsy.

Furthermore, if the medical instrument 10 is so configured as to collect the biological tissues b by drawing the fluid flowing in the gap c while supplying the fluid into the fluid lumen 23 to make the fluid flow into the gap c via the through-hole 25, it is possible to surely collect the biological tissues b adhering to the helical groove 22 formed at the distal part 21 of the main body portion 20. In particular, in the case of performing a biopsy of cancer tissues, dissemination can be surely prevented due to the movement of the biological tissues b into the gap c.

In addition, if the medical instrument 10 is so configured as to have the positioning portion 70 that defines the relative positions of the main body portion 20 and the tubular member 30 in the radial direction, the size of the gap c formed between the main body portion 20 and the tubular member 30 can be properly ensured and the fluid and the biological tissues b can be smoothly moved in the gap c.

Moreover, if the medical instrument 10 is so configured as to have the holding portion 80 that holds the main body portion 20 movably relative to the tubular member 30, introduction into a living body can be performed in the state in which the main body portion 20 is integrally assembled with the tubular member 30. Furthermore, only the main body portion 20 can be independently moved in puncture into the biological organ B with the main body portion 20. Thus, the medical instrument 10 with high usability can be provided.

Furthermore, if the holding portion 80 is formed of the first screw part 81 provided on the main body portion 20 and the second screw part 82 provided on the tubular member 30, rotating the main body portion 20 or the tubular member 30 allows the main body portion 20 to be moved in the axial direction with the amount of movement according to the amount of rotation. Because it is possible to easily adjust the amount of movement through operation at hand, the medical instrument 10 with higher usability can be provided.

In addition, in the case in which the medical instrument 10 is used to harvest the biological tissues b in the respiratory region, the main body portion 20 can be favorably stuck into an organ in the respiratory region formed of the comparatively-soft biological tissues b. Furthermore, because the number of times of bringing out the main body portion 20 to the external of the living body can be suppressed to a small number, e.g. in the case of harvesting the biological tissues b at a peripheral part of a lung, the work time can be shortened at a higher degree compared with the case of using related-art medical instruments for a biopsy.

Moreover, if the medical system 100 is constructed with the medical instrument 10, the fluid supply unit 40 that supplies a fluid into the fluid lumen 23 of the main body portion 20, and the fluid drawing unit 50 that draws the fluid existing in the gap c formed between the main body portion 20 and the tubular member 30, a medical system to efficiently harvest the biological tissues b by using the medical instrument 10 can be provided.

Although the medical instrument and the medical system according to the present invention are described above based on the embodiment, the present invention is not limited to only the configurations described in the embodiment and various modifications can be made based on contents set forth in the scope of claims.

For example, it suffices for the medical instrument 10 to include at least the main body portion 20 and the tubular member 30 and the placement of the positioning portion 70 and the holding portion 80 can be omitted. Furthermore, the medical instrument 10 and the medical system 100 can be widely applied to the respective organs of a living body and the application target thereof is not limited to only biological organs in the respiratory region.

Furthermore, although the form in which the holding portion 80 is formed of screws is described, the holding portion 80 is not limited to such a configuration. For example, the holding portion 80 can be formed by a predetermined member disposed between the main body portion 20 and the tubular member 30 like the positioning portion 70. If such a configuration is employed, inadvertent movement of the main body portion 20 and the tubular member 30 can be prevented by a friction force. Furthermore, it is also possible to move the main body portion 20 and the tubular member 30 independently of each other. Therefore, for example, the positioning portion 70 can be used also as the holding portion 80 and it is also possible to omit the placement of the holding portion 80.

It should be understood by those skilled in the art that various modifications, combinations, sub-combinations and alterations may occur depending on design requirements and other factors insofar as they are within the scope of the appended claims or the equivalents thereof.

While illustrative and presently preferred embodiments of the present invention have been described in detail herein, it is to be understood that the inventive concepts may be otherwise variously embodied and employed without departing from the spirit and scope of the invention. The appended claims are intended to be construed to include such variations and equivalents.

What is claimed is:

1. A medical instrument for harvesting biological tissues, the medical instrument comprising:

a main body portion having an elongated shape, a distal part having a helical groove formed in an outer surface of the main body portion, a fluid lumen, and a through-hole formed in the main body portion in the helical groove and in fluid communication with the fluid lumen; and a tubular member having an insertion lumen configured to moveably receive the main body portion in an axial direction, wherein a gap is formed between the tubular member and main body portion, the gap being configured to receive fluid passing between the fluid lumen of the main body portion and the tubular member via the through-hole when the main body portion is inserted in the insertion lumen, wherein the helical groove at the distal part is configured to capture biological tissue and wherein the gap is adapted to collect biological tissue when biological tissue is flushed from the helical groove by a fluid flow from the fluid lumen to the gap, wherein a fluid supply unit supplies the fluid into the fluid lumen of the main body portion.

2. The medical instrument according to claim 1, further comprising a positioning portion that is disposed between the outer surface of the main body portion and the tubular member, and which defines relative positions of the main body portion and the tubular member in a radial direction.

3. The medical instrument according to claim 1, further comprising a holding portion configured to moveably hold the main body portion relative to the tubular member.

4. The medical instrument according to claim 3, wherein the holding portion has a first screw part provided on the main body portion and a second screw part that is provided on the tubular member, the second screw part being meshed with the first screw part, and wherein rotating the main body portion or the tubular member allows the main body portion to be moved in the axial direction with an amount of movement according to an amount of rotation.

5. The medical instrument according to claim 1, wherein the medical instrument is configured for harvesting biological tissues in a respiratory region.

6. A medical system comprising: a medical instrument;

a main body portion having an elongated shape, a distal part having a helical groove formed in an outer surface of the main body portion, a fluid lumen, and a through-hole formed in the main body portion in the helical groove and in fluid communication with the fluid lumen; and a tubular member having an insertion lumen configured to moveably receive the main body portion in an axial direction, wherein a gap is formed between the tubular member and main body portion, the gap being configured to receive fluid passing between the fluid lumen of the main body portion and the gap in the tubular member via the through-hole when the main body portion is inserted in the insertion lumen, a fluid supply unit that supplies the fluid into the fluid lumen of the main body portion; and a fluid drawing unit that draws the fluid existing in the gap, wherein the helical groove at the distal part is configured to capture biological tissue and wherein the gap is adapted to collect biological tissue when biological tissue is flushed from the helical groove by a fluid flow from the fluid lumen to the gap.

7. A medical instrument for harvesting biological tissue, the medical instrument comprising:

an elongated main body portion extending axially from a proximal end to a distal end, and having a helical groove formed in an outer side surface of the main body portion, an internal central lumen extending from the proximal end toward the distal end wherein the internal central lumen is open at the proximal end and closed at the distal end, and a through-hole substantially at the proximal end extending radially from the internal central lumen to the main body portion in the helical groove, wherein the internal central lumen is in fluid communication with the through-hole:

a tubular member having an insertion lumen wherein the elongated main body portion and tubular member are sized so that a gap is defined between the tubular member and elongated main body portion, the gap being configured to receive fluid passing between the fluid lumen of the elongated main body portion and the tubular member via the through-hole when the elongated main body portion is inserted in the insertion lumen; and wherein the tubular member is configured to moveably receive the elongated main body portion in an axial direction and to rotatably receive the elongated main body portion in the insertion lumen, wherein the helical groove at the distal end is configured to capture biological tissue and wherein the gap is adapted to collect biological tissue when biological tissue is flushed from the helical groove by fluid flow from the fluid lumen to the gap, wherein a fluid supply unit supplies the fluid into the fluid lumen of the main body portion.

* * * * *